US010368857B2

(12) United States Patent
Miller et al.

(10) Patent No.: US 10,368,857 B2
(45) Date of Patent: Aug. 6, 2019

(54) METHODS AND DEVICES FOR KNOTLESS SUTURE ANCHORING

(71) Applicant: Medos International Sárl, Le Locle (CH)

(72) Inventors: Gerome Miller, Randolph, MA (US); Justin M. Piccirillo, Uxbridge, MA (US); Benjamin Cleveland, Milford, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 0 days.

(21) Appl. No.: 15/457,944

(22) Filed: Mar. 13, 2017

(65) Prior Publication Data
US 2018/0256148 A1 Sep. 13, 2018

(51) Int. Cl.
A61B 17/04 (2006.01)

(52) U.S. Cl.
CPC .... *A61B 17/0401* (2013.01); *A61B 2017/044* (2013.01); *A61B 2017/0409* (2013.01); *A61B 2017/0412* (2013.01); *A61B 2017/0414* (2013.01); *A61B 2017/0445* (2013.01); *A61B 2017/0453* (2013.01); *A61B 2017/0464* (2013.01); *A61B 2017/0496* (2013.01)

(58) Field of Classification Search
CPC ............... A61B 17/04; A61B 17/0401; A61B 2017/0409; A61B 2017/0414; A61B 2017/0437; A61B 2017/0446; A61B 2017/0412; A61B 2017/0451; A61B 2017/0464
USPC ........................................................ 606/232
See application file for complete search history.

(56) References Cited

U.S. PATENT DOCUMENTS

| 5,649,963 A | 7/1997 | McDevitt |
| 5,906,632 A | 5/1999 | Bolton |
| 6,527,794 B1 | 3/2003 | McDevitt et al. |
| 7,780,701 B1 | 8/2010 | Meridew et al. |
| 7,993,369 B2 | 8/2011 | Dreyfuss |

(Continued)

FOREIGN PATENT DOCUMENTS

| WO | WO-2009076526 A1 | 6/2009 |
| WO | WO-2013169905 A1 | 11/2013 |

(Continued)

OTHER PUBLICATIONS

Extended European Search Report for EP App. No. 18161239.1 dated Aug. 14, 2018 (7 pages).

(Continued)

*Primary Examiner* — George J Ulsh

(57) ABSTRACT

Methods and devices are provided for securing tissue to bone. A surgical system can include a guide, a suture anchor including a sheath and a screw, a first driver shaft, and a second driver shaft. The first driver shaft can be configured to be removably received within a lumen of the guide such that an awl tip thereof extends beyond a distal end of the sheath. The sheath and the guide can have first and second side openings, respectively, that can receive at least one suture therethrough. The second driver shaft can be configured to be removably received within the lumen of the guide when the first elongate shaft is removed therefrom, the second driver shaft having a distal driver member configured to be removably received within a proximal channel formed in the screw to drive the screw into mating engagement with the sheath.

6 Claims, 17 Drawing Sheets

(56) References Cited

U.S. PATENT DOCUMENTS

| | | |
|---|---|---|
| 8,202,295 B2 | 6/2012 | Kaplan |
| 8,469,998 B2 | 6/2013 | Sojka et al. |
| 8,523,902 B2 | 9/2013 | Heaven et al. |
| 8,974,494 B2 | 3/2015 | Paulk et al. |
| 9,265,601 B2 | 2/2016 | Bojarski et al. |
| 9,277,910 B2 | 3/2016 | Nason et al. |
| 9,295,460 B2 | 3/2016 | Hoof et al. |
| 2007/0005068 A1 | 1/2007 | Sklar |
| 2009/0292321 A1 | 11/2009 | Collette |
| 2011/0112576 A1 | 5/2011 | Nguyen et al. |
| 2013/0035721 A1 | 2/2013 | Brunelle |
| 2013/0267998 A1 | 10/2013 | Vijay et al. |
| 2013/0338710 A1 | 12/2013 | Heaven et al. |
| 2014/0277150 A1 | 9/2014 | Jones et al. |
| 2014/0364906 A1 | 12/2014 | Palese et al. |
| 2015/0018878 A1 | 1/2015 | Rizk et al. |
| 2016/0128682 A1 | 5/2016 | Konrath et al. |
| 2018/0256149 A1 | 9/2018 | Gustafson et al. |

FOREIGN PATENT DOCUMENTS

| | | |
|---|---|---|
| WO | WO-2015127057 A1 | 8/2015 |
| WO | WO-2017003442 A1 | 1/2017 |

OTHER PUBLICATIONS

Extended European Search Report for EP App. No. 18161276.3 dated Aug. 10, 2018 (7 pages).

METHODS AND DEVICES FOR KNOTLESS SUTURE ANCHORING

FIELD

The present disclosure relates generally to methods and devices for attaching tissue to bone.

BACKGROUND

Tearing of, or the complete or partial detachment of ligaments, tendons and/or other soft tissues from their associated bones within the body are commonplace injuries, particularly among athletes. Such injuries generally result from excessive stresses being placed on these tissues. By way of example, tissue tearing or detachment may occur as the result of an accident such as a fall, over-exertion during a work-related activity, or during the course of an athletic event. In the case of tearing or a partial or complete detachment of soft tissue from a bone, surgery is typically required to reattach the soft tissue (or a graft tissue) to the bone.

Numerous devices have been used to secure soft tissue to bone. Examples of such devices include screws, tacks, staples, suture anchors, and suture alone. In soft tissue repair or re-attachment procedures utilizing suture anchors, an anchor-receiving hole is drilled into bone at the desired point of fixation or tissue re-attachment, and a suture anchor is deployed into the hole using an appropriate installation tool. A suture, coupled to the anchor and passed through or around the soft tissue, thus becomes effectively locked to the bone, which secures the soft tissue to the bone.

During a suture anchoring procedure, it can be challenging to deploy the suture anchor into the anchor-receiving hole. Further, existing suture anchors and inserter devices used to insert the anchors into bone may have certain disadvantages that complicate their use and/or impose certain undesirable limits. Also, procedures that require the suture to be tied into a knot can be time-consuming and cumbersome due to inherent space constraints, which can complicate a surgery.

Accordingly, there is a need for improved methods and systems for attaching tissue to bone.

SUMMARY

In one aspect, a surgical system is provided that in some embodiments includes a guide having a lumen extending therethrough, a suture anchor including a sheath and a screw, a first driver shaft, and a second driver shaft. The sheath has a first side opening and the screw is configured to be received within a lumen formed in the sheath so as to mate with the sheath. The first driver shaft is configured to be removably received within the lumen of the guide such that an awl tip thereof extends beyond a distal end of the sheath. The second driver shaft is configured to be removably received within the lumen of the guide after the first driver shaft is removed therefrom, the second driver shaft having a distal driver member configured to be removably received within a proximal channel formed in the screw to drive the screw into mating engagement with the sheath.

The surgical system can vary in many different ways. For example, the distal driver member can have an outer diameter that is less than an outer diameter of an intermediate portion of the second driver shaft having the distal driver member extending distally therefrom. As another example, the first driver shaft can have a proximal portion, an intermediate portion, and a distal portion having the awl tip, the central portion having an outer diameter that is less than an outer diameter of the proximal portion and that is greater than an outer diameter of the distal portion.

In at least some embodiments, the guide has a second side opening. The second side opening can communicate with the first side opening via the lumen of the guide.

In at least some embodiments, the screw has external threads formed thereon that are configured to mate with corresponding threads within the lumen of the sheath. In at least some embodiments, the second driver shaft is configured to rotatably drive the screw into the lumen of the sheath. In at least some embodiments, the first driver shaft has a proximal handle coupled thereto.

In another aspect, a method for performing a surgical repair is provided that in some embodiments includes inserting a distal end of a first driver into a bone, the first driver extending through a proximal channel in a sheath portion of an implantable suture anchor and through a lumen of a guide removably coupled proximally to the sheath portion, the sheath portion and the guide having a suture extending through the lumen and the proximal channel and between first and second openings extending through sides of the sheath portion and the guide, respectively. The method further includes removing the first driver from the proximal channel and the lumen, and then inserting a distal driver member of a second driver through the lumen of the guide and into the proximal channel of the sheath portion, the distal driver member having a screw portion of the suture anchor coupled distally thereto, wherein the insertion causes the screw portion to be driven distally into the proximal channel and the suture to be secured between an outer wall of the sheath portion and the bone and between an outer wall of the screw portion and an inner wall of the sheath portion.

The method can vary in many different ways. For example, inserting the distal driver member through the lumen and into the proximal channel of the sheath portion can include rotating the second driver to cause the distal driver member to insert the screw portion into the proximal channel of the sheath portion. As another example, the suture can be engaged using the implantable suture anchor such that it extends between the bone and an outer wall of a proximal portion of the sheath portion, along a proximal inner wall of the first opening, and between an inner wall of the proximal portion of the sheath portion and an outer wall of the screw portion. As a further example, the screw portion received within the proximal channel of the sheath portion can cause expansion of the sheath portion.

In at least some embodiments, the method further includes tensioning the suture while inserting the distal end of the first driver into the bone. In at least some embodiments, the method further includes tensioning the suture while inserting the distal driver member through the lumen of the guide and into the proximal channel of the sheath portion. In at least some embodiments, the screw portion being received within the proximal channel of the sheath portion causes expansion of the sheath portion.

BRIEF DESCRIPTION OF THE DRAWINGS

The present disclosure will be more fully understood from the following detailed description taken in conjunction with the accompanying drawings, in which.

DETAILED DESCRIPTION

Figure 1:
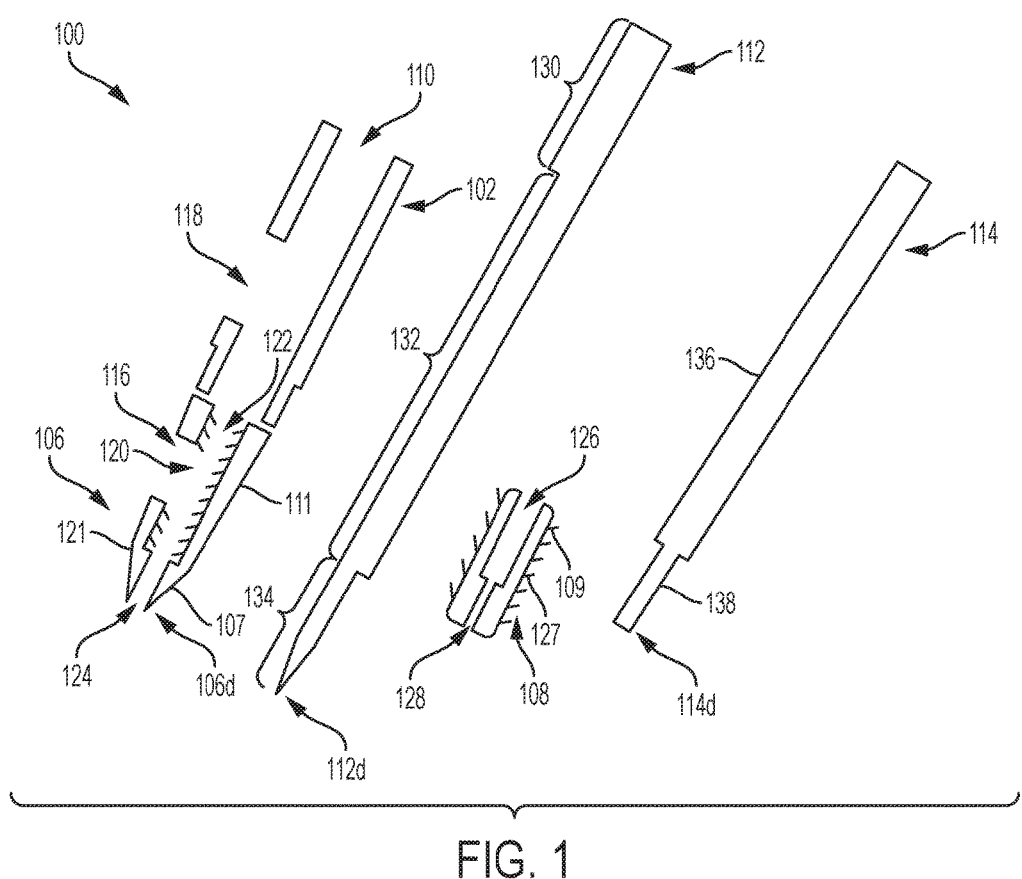
FIG. 1 is an exploded view of one embodiment of a surgical system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various methods and devices are provided for attaching tissue to bone. In some embodiments, a surgical system for attaching tissue to bone includes a guide, a suture anchor, a first driver shaft and a second driver shaft. The suture anchor includes a cannulated sheath portion and a screw portion configured to be received within a proximal lumen formed in the sheath portion so as to mate with the sheath portion. The screw portion of the suture anchor is configured to be received within the sheath portion of the suture anchor and it can mate with the sheath portion in various ways. For example, in some embodiments, the screw portion has external threads formed thereon that are configured to mate with corresponding threads within at least a portion of the proximal lumen of the sheath portion.

The first driver shaft is configured to drive the anchor's sheath portion into a bone, and it is configured to be removably received within a lumen extending through the guide such that an awl tip of the first driver shaft extends beyond a distal end of the anchor's sheath portion. In the described embodiments, the lumen of the guide can receive the first driver shaft or the second driver shaft. Thus, the second driver shaft is configured to be removably received within the lumen of the guide when the first driver shaft is removed therefrom. The second driver shaft has a distal driver member configured to be removably received within a proximal channel formed in the screw portion of the anchor to drive the screw portion into mating engagement with the sheath portion of the anchor. For example, the second driver shaft can be configured to rotatably drive the anchor's screw portion into the proximal lumen of the sheath portion.

A method for performing a surgical repair to attach soft tissue to bone is also provided. The method in some embodiments includes inserting a distal end of a first driver into a bone, the first driver extending through a proximal channel in a sheath portion of an implantable suture anchor and through a lumen of a guide removably coupled proximally to the sheath portion. The sheath portion and the guide have a suture extending through the proximal channel of the sheath portion and the lumen of the guide and between first and second openings extending through sides of the sheath portion and the guide, respectively. The method further includes removing the first driver from the proximal channel in the sheath portion and the lumen of the guide, and inserting a distal driver member of a second driver through the lumen of the guide and into the proximal channel of the sheath portion. The distal driver member of the second driver has a screw portion of the suture anchor coupled distally thereto, and the insertion of the second driver through the guide and into the sheath portions' proximal channel causes the screw portion to be driven distally into the proximal channel of the anchor's sheath portion, and the suture to be secured between an outer wall of the sheath portion and the bone and between an outer wall of the screw portion and an inner wall of the sheath portion. Thus, the suture is pinched in two ways, which may help hold the suture in place and hence help hold soft tissue coupled to the suture relative to the bone.

In some embodiments, a surgical system can include a driver device and a suture anchor assembly including a sheath and a screw or plug. The driver device includes an inner shaft extending through at least a portion of a lumen in the driver device and through the sheath so as to protrude distally beyond a distal end of the sheath. The driver device also includes an outer shaft and a driver shaft extending distally therefrom. The driver shaft can have a first side opening, the outer shaft can have a second side opening, and the sheath has a third side opening. The first, second, and third openings can communicate such that a suture (which can include multiple sutures) can be passed therethrough. The driver shaft is configured to be removably coupled to the plug such that the driver shaft extends through a lumen extending longitudinally through the plug, with the plug being disposed within a lumen of the sheath. The driver shaft can be rotated to cause the plug to be driven proximally within the sheath's lumen so as to occlude the third opening in the sheath and to thus secure the suture between an outer wall of the sheath and the bone and between an outer wall of the plug and an inner wall of the sheath. In some embodiments, such a surgical system can be configured such that the driver shaft can be rotated to cause the plug to be driven distally within the sheath's lumen.

Multiple sutures can be coupled to a surgical system as described herein and used to attach soft tissue to bone. A size of the first side opening formed in the anchor and a size of the second side opening formed in the guide can be such that multiple sutures can extends between the openings. In use, tension is maintained on the suture while the first driver is removed from the proximal channel in the sheath portion and the lumen of the guide. The surgical system is configured so as to allow sutures to be tensioned to a desired level, and the tensioning can be adjusted. The tension on the sutures can be easily maintained, even if a large number of sutures are used.

FIG. 1 illustrates one embodiment of a surgical system 100 that includes a guide 102 which can be cannulated, an implantable suture anchor 104 including a cannulated sheath portion or sheath 106 and a screw portion or screw 108. The cannulated guide 102 has a lumen 110 extending therethrough and the guide 102 is configured to allow other components to pass to a suture insertion site. As shown in FIG. 1, the surgical system 100 also includes a first driver shaft or driver 112 configured to be removably received within the lumen 110 of the guide 102 such that a distal tip 112 d thereof extends beyond a distal end 106 d of the sheath 106. The surgical system 100 also has a second driver shaft or driver 114 configured to be removably received within the lumen 110 of the guide 102 when the first driver shaft 112 is removed from the lumen 110, as discussed in more detail below.

The surgical system 100 can be provided as a kit including at least the guide 102, the implantable suture anchor 104, and the first and second drivers 112, 114. In use, the first driver 112 can be inserted into the guide 102, and the second driver 114 can be inserted into the guide after the first driver 112 is removed from the guide 102, as discussed in detail below.

FIG. 1 illustrates that the sheath 106 has a first side opening 116 formed through a side wall thereof and that the guide 102 has a second side opening 118 formed through a side wall thereof. When the guide 102 is disposed proximally to the sheath 106, the first and second side openings 116, 118 are disposed on the same side of the lumen 110, as shown in FIG. 1. The openings 116, 118 can communicate via a lumen 120 extending through the sheath 106 with which the first side opening 116 communicates, and via the lumen 110 in the guide 102 with which the second side opening 118 communicates. The openings 116, 118 are configured to receive therethrough one or more sutures, as discussed below. In the illustrated embodiment, the sheath 106 has the lumen 120 extending longitudinally therethrough that is configured to receive the first driver shaft 112 and then receive the screw 108.

The guide 102 can have various configurations. The guide 102 can be generally a tubular component that, in some embodiments, can have its distal end removably coupled to the proximal end of the sheath 106. The sheath 106 can have various configurations. As shown in FIG. 1, the sheath 106 can be generally distally tapered and having a more tapered distal portion 107 terminating at the sheath's distal end 106d. In at least some embodiments, the sheath 106 can have external threads or other bone-engaging features formed thereon that facilitate engagement of the suture anchor 104 with bone. The lumen 120 of the sheath 106 is configured to receive the screw 108 after the first driver shaft 112 has been removed from the lumen 120. The sheath 106 can be coupled to the first driver shaft 112 such that the first driver shaft 112 is configured to insert the sheath 106 into a bone. The distal tip 112d of the first driver shaft 112 can be used to form a hole in the bone that can be expanded as the distal portion of the sheath 106 is inserted into the bone. As shown, the lumen 120 includes a proximal channel or portion 122 terminating at a distal shoulder 121 within the lumen 120 and having a larger inner diameter than a distal portion 124 of the lumen 120 extending from the distal shoulder 121 to the distal end 106d. In use, the proximal portion 122 is configured to receive therein the screw 108, as discussed in more detail below.

The screw portion 108 can also have various configurations. For example, it can be generally rectangular or semi-cylindrical and can have a proximal channel 126 formed therein. In the illustrated embodiment, the screw 108 also has a narrower distal channel 128 communicating with and extending from the proximal channel 126, as shown in FIG. 1. The distal channel 128 can be used for outflow of blood and/or other fluids. However, in some embodiments, the screw 108 may not include a distal channel and instead have a closed distal tip so as to not be cannulated. In at least some embodiments, the screw 108 has an external bone-engaging features such as external threads 109 formed thereon that are configured to mate with corresponding threads 111 formed on at least a portion of an interior wall defining the lumen 120 of the sheath 106. The threads 111 can be formed within the proximal portion 122 of the lumen 120, whereas the distal portion 124 of the lumen 120 is free of threads.

The first driver 112 can have various configurations. In the illustrated embodiment, the first driver 112 is a shaft configured to be inserted into bone to initiate a hole. In the example illustrated, the first driver 112 has a proximal portion 130, an intermediate portion 132, and a distal portion 134 having the distal tip 112d. As shown in FIG. 1, the intermediate portion 132 has an outer diameter that is less than an outer diameter of the proximal portion 130 and that is greater than an outer diameter of the distal portion 134. This configuration of the first driver 112 may allow a suture to be passed between the sheath 106 and the guide 102 when the first driver 112 is inserted through the guide 102.

Figure 2A:
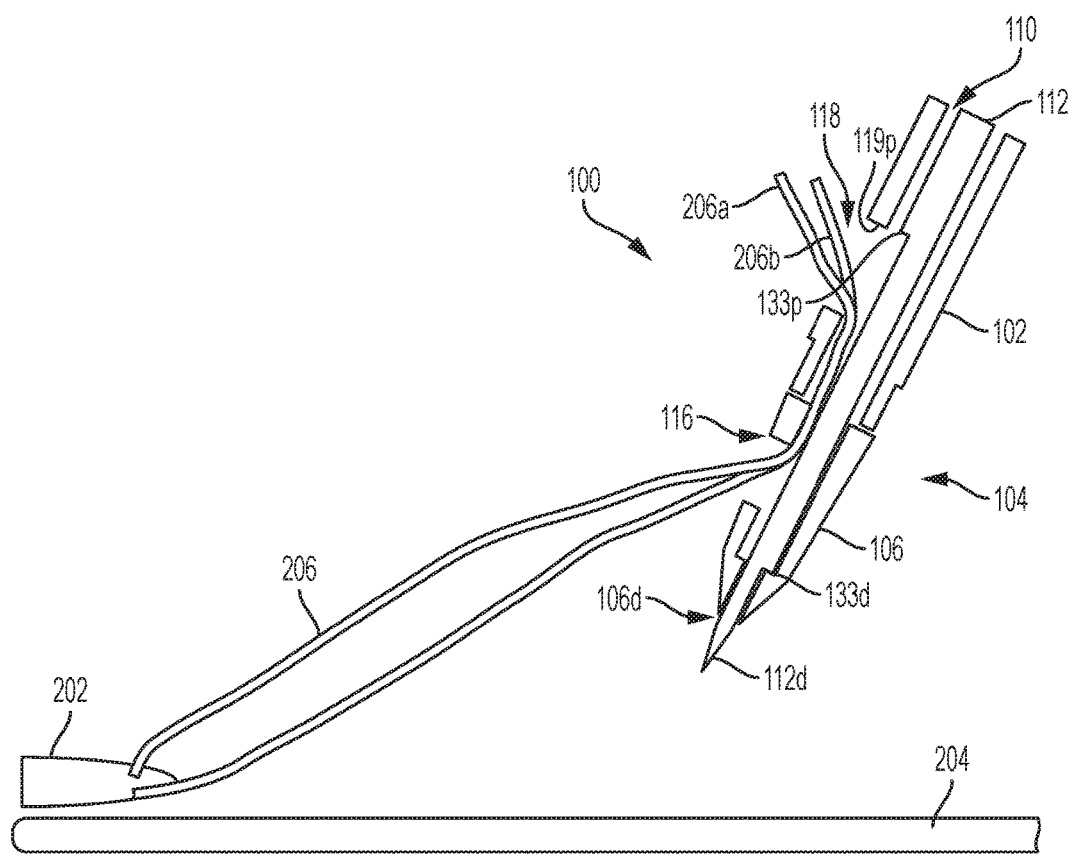
FIG. 2A is perspective view of the surgical system of FIG. 1 in an assembled configuration and near bone.

In an assembled configuration, as shown in FIG. 2A, the first driver 112 is removably received within the lumen 110 of the guide 102 such that the first driver's distal awl tip 112d extends beyond the distal end 106d of the sheath 106. As also shown in FIG. 2A, the first driver 112 is received within the lumen 110 such that a proximal end 133p of the intermediate portion 132 of the first driver 112 aligns with a proximal end 119p of the side opening 118 formed in the guide 102, and such that a distal end 133d of the intermediate portion 132 abuts the distal shoulder 121 of the sheath's lumen 120. The first driver 112 fits within the guide 102 such that the first and second side openings 116, 118 communicate via the lumen 110 in the guide 102. In this way, a suture can be passed through the first opening 116, through the lumen 110, and through the second opening 118. The distal portion 134 of the first driver 112 is received within the distal portion 124 of the sheath's lumen 120. It should be appreciated, however, that the first driver 112 can have various other configurations. For example, in some embodiments, the proximal and intermediate portions 130, 132 may not be separate portions and the driver 112 can have a proximal portion and can have a distal portion with an awl tip.

The second driver 114 configured to drive the screw 108 into the lumen 120 of the sheath 106 also can also have various configurations. In the illustrated embodiment, the second driver 114 has a proximal portion 136 and a distal driver member 138 extending distally from the proximal portion 136 and terminating at a distal end 114d of the second driver 114, as shown in FIG. 1. The distal driver member 138, which can have an outer diameter less than an outer diameter of the proximal portion 136, is configured to be removably received within the proximal channel 126 formed in the screw 108 to drive the screw 108 into mating engagement with the sheath 106, as discussed below. As shown in FIG. 2A, the distal driver member 138 can be inserted in the proximal channel such that the distal end 114d abuts a distal shoulder 127. The distal driver member 138 can be configured to be removably received within the proximal channel 126 via, for example, a friction fit.

The surgical system 100 can have other components that are not shown in FIG. 1. For example, the system 100 can include a threader tab or loop configured to assist in passing sutures through the openings 116, 118 in the sheath 106 and the guide 102. For another example, the surgical system 100 can include a handle for the first driver 112. For yet another example, the surgical system 100 can include one or more sutures to be used to attach tissue to bone.

The components of the surgical system 100 can have various dimensions. For example, in at least some embodiments, the sheath 106 can have an outer diameter in a range from about 2 mm to about 8 mm. In at least one embodiment, the sheath 106 can have a length of about 16 mm. In at least some embodiments, the screw 108 can have an outer diameter in a range from about 1 mm to about 7 mm, and a length in a range from about 3 mm to about 15 mm. It should be appreciated that the sheath 106 and the screw 108 can have any other dimensions.

The surgical system 100, or other surgical system described herein, can be used to perform a surgical repair method involving reattachment of soft tissue to bone or attaching a graft tissue to bone. For example, the system can be used in reattaching a tendon (e.g., the supraspinatus tendon) to bone (e.g., the humeral head) in a rotator cuff repair procedure. The repair procedure can be a lateral-row rotator cuff repair or other procedure. The described techniques may simplify deployment of components of the surgical system, allow control of suture tension, provide for appropriate suture fixation, and/or allow a large number of sutures to be used. A lateral-row rotator cuff repair or other procedure may thus be performed in a more efficient manner. In addition, the described techniques can also be used for other shoulder repair procedures, as well as for knee and other joint repair procedures requiring soft tissue attachment to associated bone.

FIGS. 2A-2H illustrate one embodiment of a method for performing a surgical repair using the system 100 of FIG. 1, though other systems can be similarly used. As mentioned above, FIG. 2A shows the surgical system 100 in the assembled configuration that can be used to attach soft tissue 202 to bone 204.

In the configuration of the surgical system 100 in FIG. 2A, the first driver 112 extends through the lumen 110 in the guide 102 and has the sheath 106 coupled distally thereto. In particular, the first driver 112 is removably received within the lumen 110 of the guide 102 such that the tip 112d extends beyond the distal end 106d of the sheath 106. As also shown, the sheath 106 and the guide 102 have a suture 206 extending through the lumen 110 of the guide 102 and the lumen 120 in the sheath 106 and between first and second openings 116, 118 extending through sides of the sheath 106 and the guide 102, respectively. In particular, as shown, the suture 206, which is passed through or otherwise coupled to the tissue 202, extends through the sides of the sheath 106 and the guide 102 and through the first and second openings 116, 118 such that terminal end portions 206a, 206b of the suture 206 extend out of the side opening 118 formed in the guide 102. The inner surface of the lumen 120 in the sheath 106 is threaded, which facilitates engagement of the suture. It should be appreciated that a single suture 206 is shown by way of example only, as multiple sutures can be used to couple the tissue 202 to the bone 204.

Figure 2B:
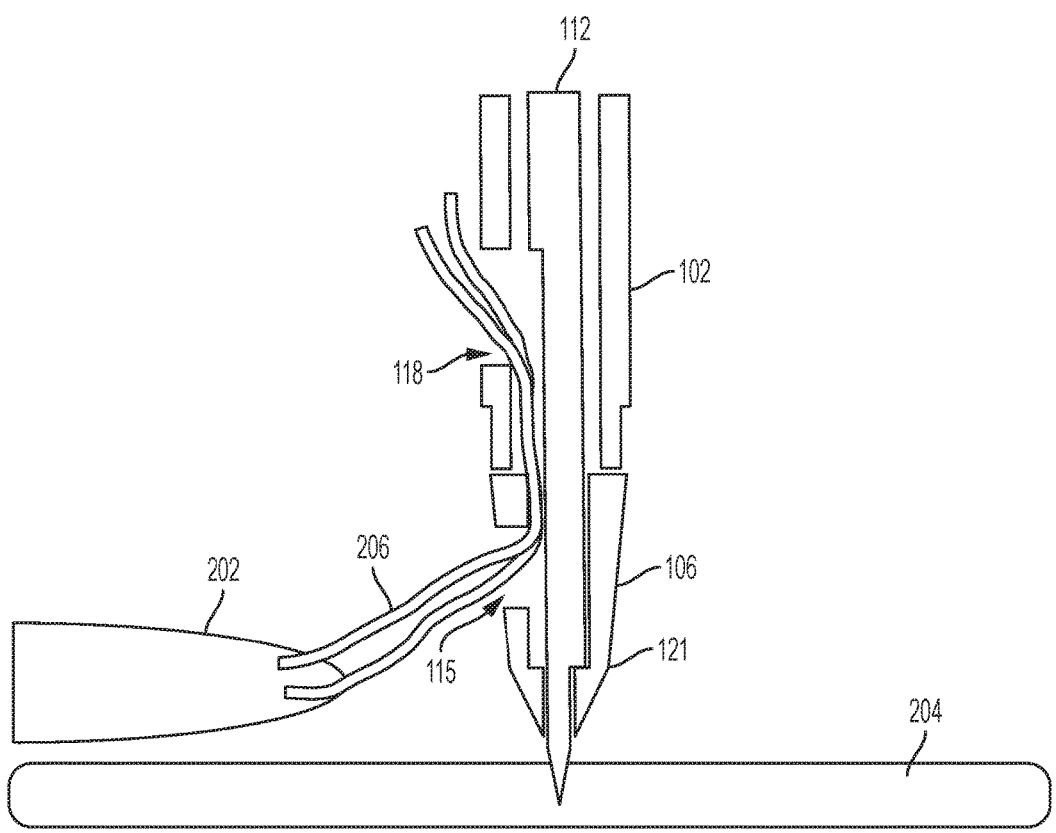
FIG. 2B illustrates the surgical system of FIG. 2A, showing a distal end of the first driver initiating a hole in the bone.

As shown in FIG. 2B, the illustrated method for performing a surgical repair involves inserting the distal end or distal awl tip 112d of the first driver 112, which extends beyond the distal end 106d of the sheath 106, into the bone 202. In FIG. 2B, the first driver 112 is shown to initiate a hole in the bone 204 at a desired location of tissue attachment. The first driver 112 is thus configured as a self-punching driver configured to initiate the bone hole, and no additional instruments are required for this purpose.

Figure 2C:
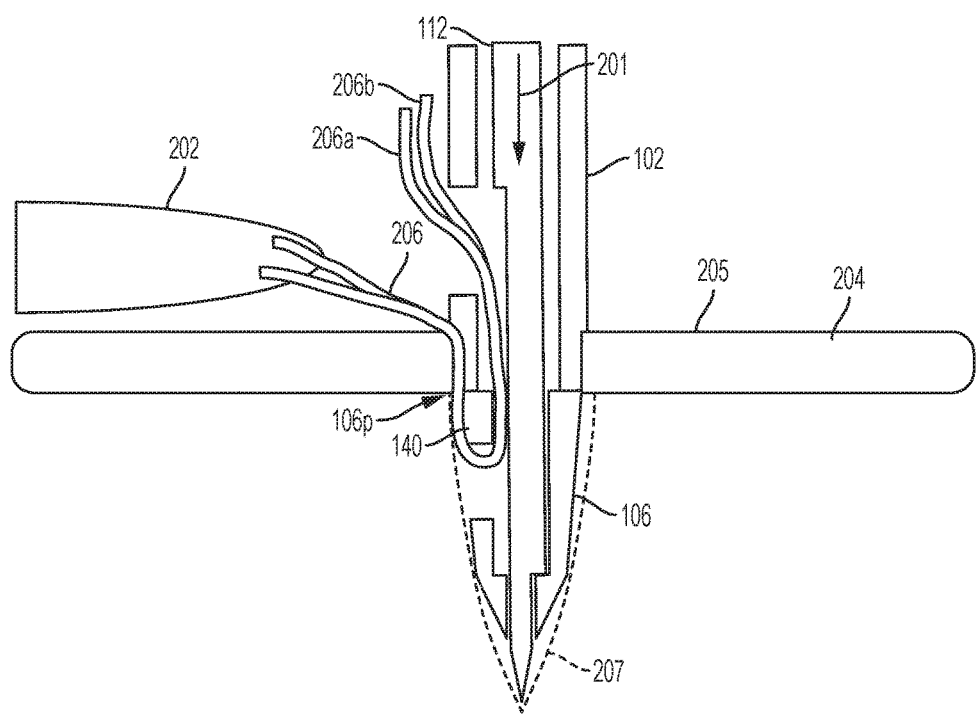
FIG. 2C illustrates the surgical system of FIG. 2B, showing the distal end of the first driver driven distally into the bone.

FIG. 2C illustrates the first driver 112 with the sheath 106 coupled thereto driven further distally, as schematically shown by an arrow 201, to insert the first driver 112 deeper into the bone 204 to form a bone hole 207. In this embodiment, when the first driver 112 is inserted deeper into the bone 204, a proximal end 106p of the sheath 106 is disposed below a surface 205 of the bone 204. However, in other embodiments, the proximal end 106p of the sheath 106 can be disposed at or above the surface 205 of the bone 204. Although not shown in FIG. 2C, the first driver 112 with the sheath 106 can be driven into the bone 204 using a mallet or other instrument. The suture 206 can be tensioned while the first driver 112 with the sheath 106 is being inserted into the bone. The suture 206 is passed through the side opening 116 in the sheath 106 such that the suture 206 is disposed between an outer wall of the guide 102 and an outer wall 140 of the sheath 106 and the bone 204. The suture 206 further extends through the lumen 110 in the guide 102 and through the second side opening 118 formed in the guide 102.

Figure 2D:
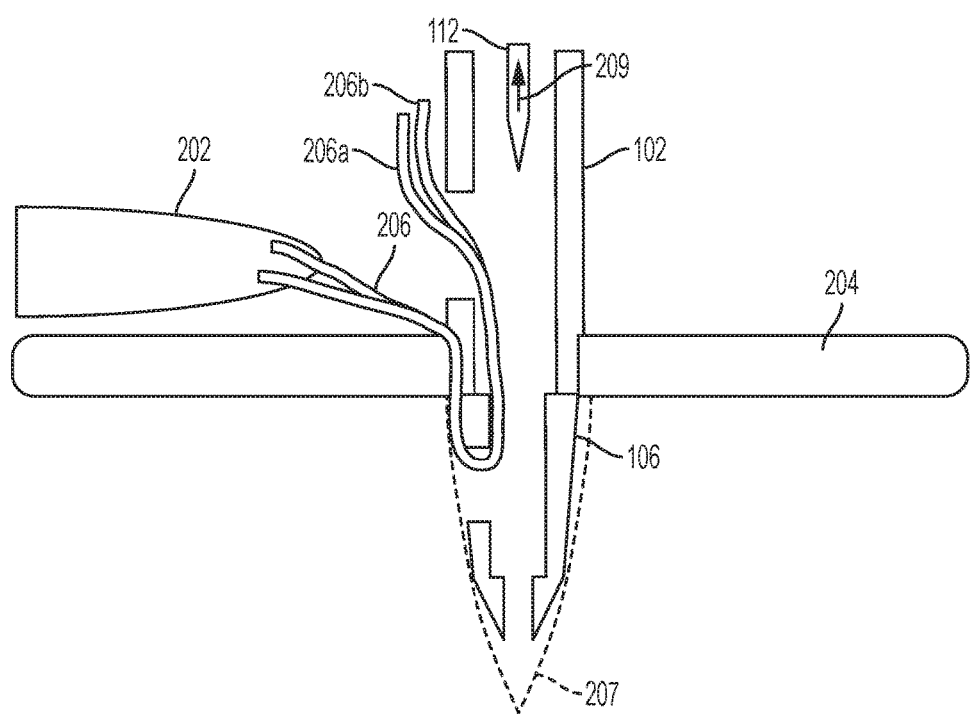
FIG. 2D illustrates the surgical system of FIG. 2C, showing the first driver being removed.

Once the sheath 106 of the anchor 104 is inserted into the bone 204 to the desired depth (e.g., a sub-cortical depth), the first driver 112 can be removed, as schematically shown by an arrow 209 in FIG. 2D indicating that the driver 112 is being retracted proximally. Before the first driver 112 and while the first driver 112 is being retracted proximally, the terminal end portions 206a, 206b of the suture 206 can be tensioned. Because the suture 206 has not yet been fixed, tensioning of the suture 206 to a desired level can be easily achieved. The first driver 112 is removed from the lumen 110 extending through the guide 102 and from the lumen 120 in the sheath 106. FIG. 2D shows only a distal portion of the first driver 112.

Figure 2E:
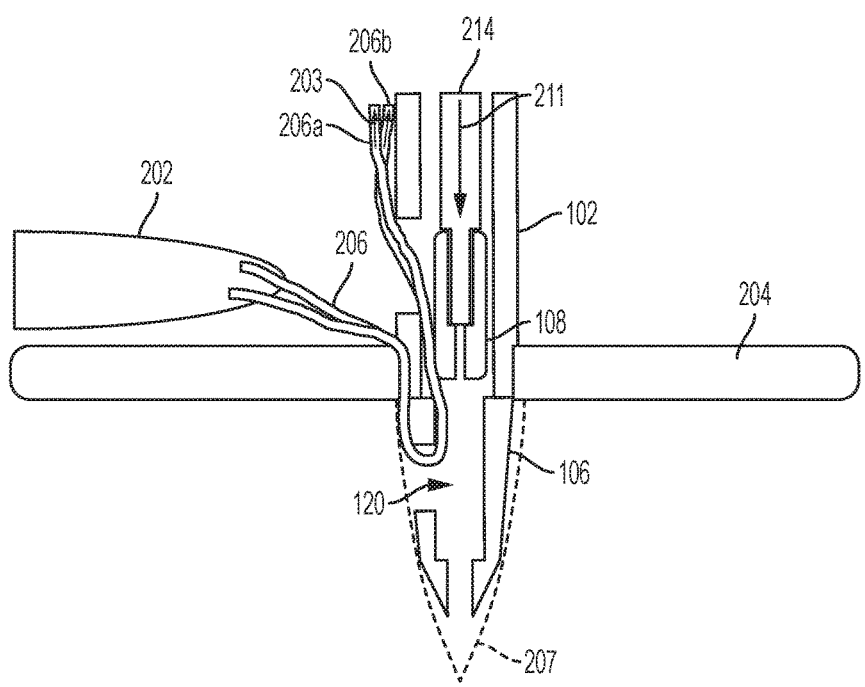
FIG. 2E illustrates the surgical system of FIG. 2D, showing a second driver with a screw near a sheath.

After the first driver 112 is removed, the distal driver member 138 of the second driver 114 having the screw 108 coupled thereto can be inserted through the lumen 110 of the guide 102 and into the lumen 120 in the sheath 106, as shown in FIG. 2E. The guide 102 assists the second driver 114 having the screw 108 coupled thereto to locate the sheath 106 and insert the screw 108 into the sheath's lumen 120. It should be appreciated, however, that in some embodiments, the guide 102 may not be present and can instead be removed before the screw 108 is inserted into the sheath 106.

The distal driver member 138 of the second driver 114 can be releasably coupled to the screw 108 in any suitable manner. For example, the distal driver member 138 can be press-fit or otherwise removably inserted into the lumen 126 of the screw 108. As schematically shown in FIG. 2E by arrows 203, the terminal end portions 206a, 206b of the suture 206 are tensioned while the second driver 114 with the screw 108 is being inserted (e.g., pushed) into the proximal lumen 120 of the sheath 106. The described system 100 allows having control over the degree of tensioning of the suture.

Figure 2F:
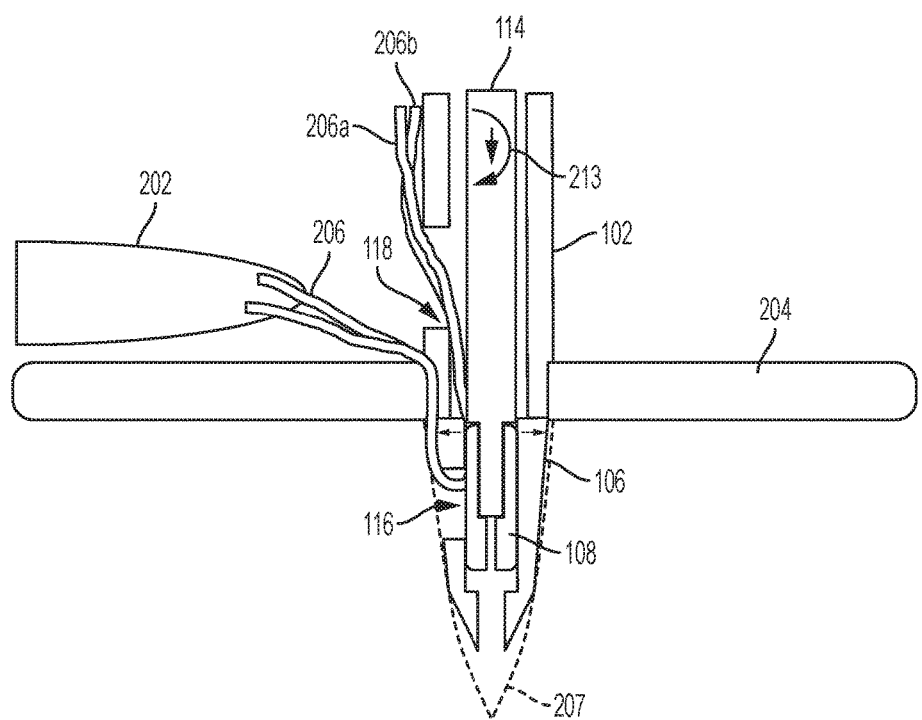
FIG. 2F illustrates the surgical system of FIG. 2E, showing the second driver with the screw inserted into the sheath.

The second driver 114 is moved distally, as schematically shown by an arrow 211, and drives the screw 108 distally into the lumen 120 of the sheath 106. In at least some embodiments, the screw 108 has the threads 109 formed on its outer wall and configured to mate with threads 111 formed on at least a portion of the interior wall defining the lumen 120 of the sheath 106. As shown in FIG. 2F, the second driver 114 can be rotated, as schematically shown by an arrow 213, to cause the screw 108 to enter the lumen 120 of the sheath 106. In the illustrated embodiment, the screw 108 is threaded into the lumen 120 of the sheath 106 such that the thread 109 formed on the screw 108 mates with the corresponding thread 111 of the sheath 106. As shown in FIG. 2F, the screw 108 is inserted into the lumen 120 of the sheath 106 such that the screw 108 occludes the opening 116 in the side wall of the sheath 106. In this embodiment, the screw 108 is shown to be inserted into the sheath 106 such that the screw's distal end is offset from the distal shoulder 121 within the lumen 120. However, in other embodiments, the screw can be positioned so as to abut the distal shoulder 121 within the lumen 120. In some embodiments, the guide 102 has a window that allows viewing of the second driver 114 as it is rotated within the guide 102. As the screw 108 is inserted into the sheath 106, the screw 108 can cause the sheath 106 to expand and thus engage further with the bone in the bone hole 207. The suture 206 is being trapped between the screw 108 and the sheath 106.

Figure 2G:
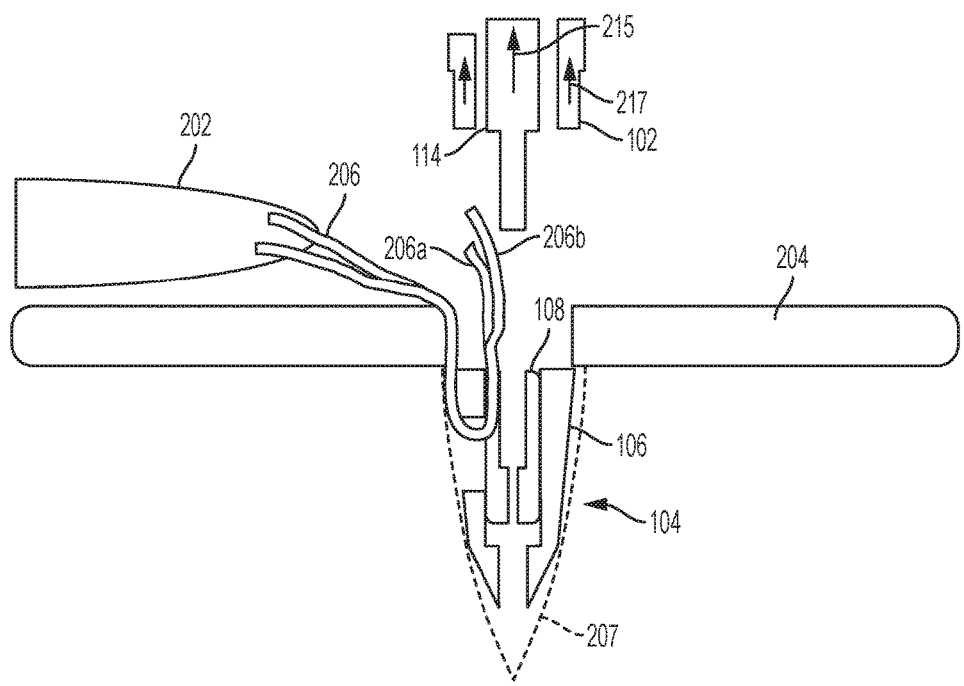
FIG. 2G illustrates the surgical system of FIG. 2F, showing the second driver and the guide being removed.
Figure 2H:
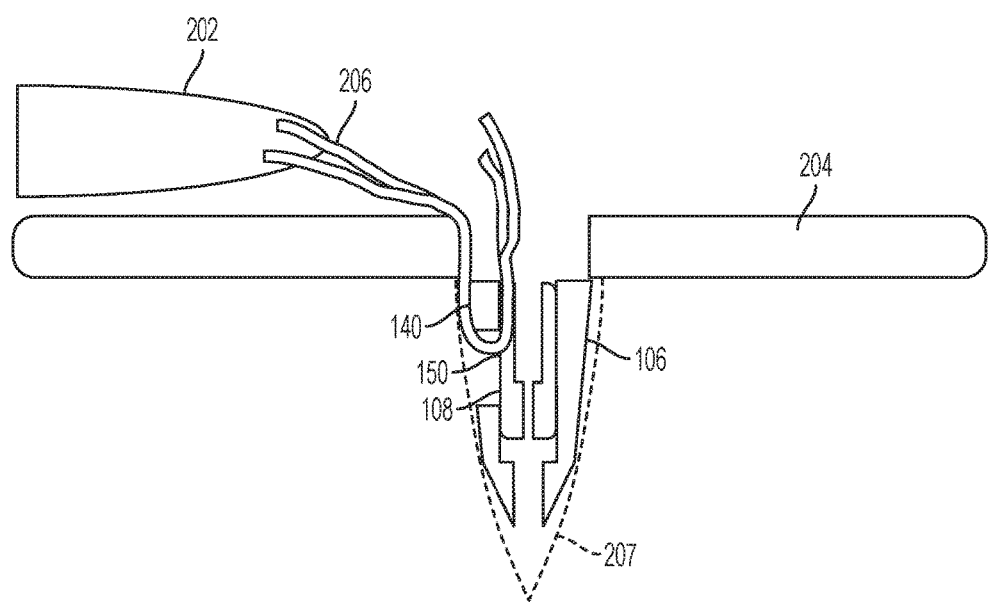
FIG. 2H illustrates the surgical system of FIG. 2G, showing a suture secured.

As shown in FIG. 2G, once the screw 108 is inserted into the sheath 106, the second driver 114 can be removed, as schematically shown by an arrow 215. The guide 102 is also removed, as schematically shown by arrows 217. As a result, as shown in FIG. 2H, the suture 206 is secured between the outer wall 140 of the sheath 106 and the bone 204 and between an outer wall 150 of the screw 108 and an inner wall 142 of the sheath 106. In this way, the suture anchor 104 secures the suture 206 in the bone 204, thereby securing the tissue 202 coupled to the suture 206 to the bone 204. If desired, the terminal end portions 206a, 206b of the suture 206 can be trimmed.

The disclosures provided herein can have a number of advantages. For example, having a second driver configured to fit within a lumen of a screw may allow using a screw that is thicker at a distal end thereof. For another example, the screw may not need to be fully cannulated, which may improve its strength. For yet another example, as discussed above, improved control over suture tensioning may be achieved.

Figure 3:
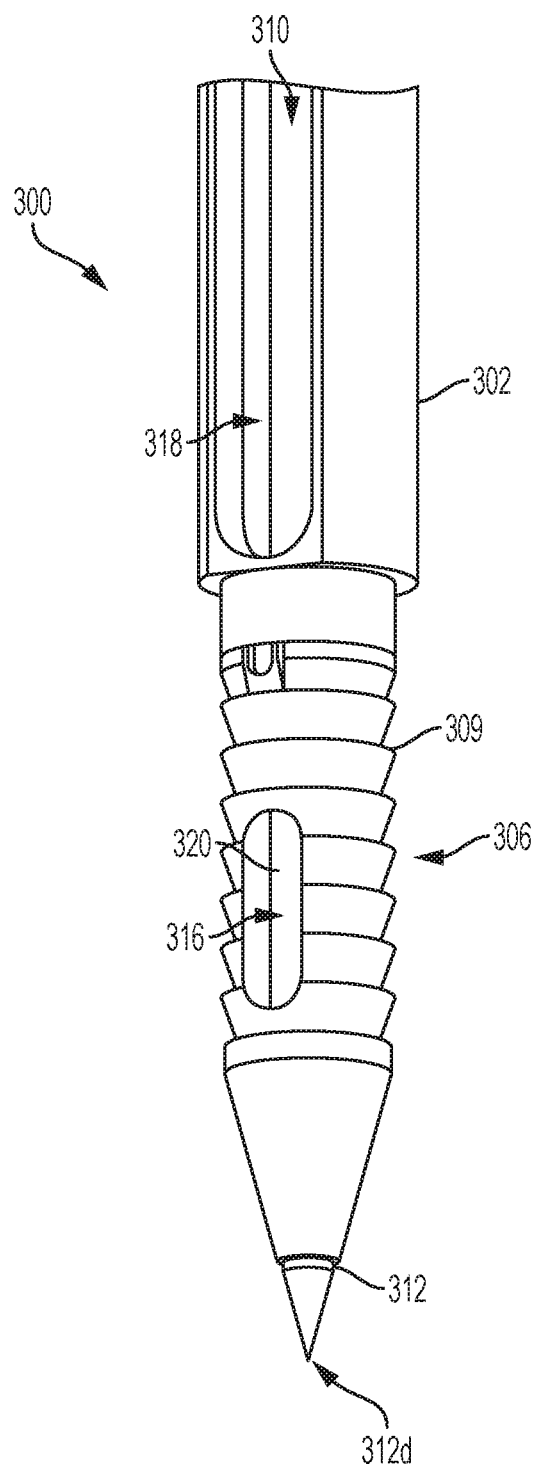
FIG. 3 is a perspective view of a portion of one embodiment of another surgical system.
Figure 4:
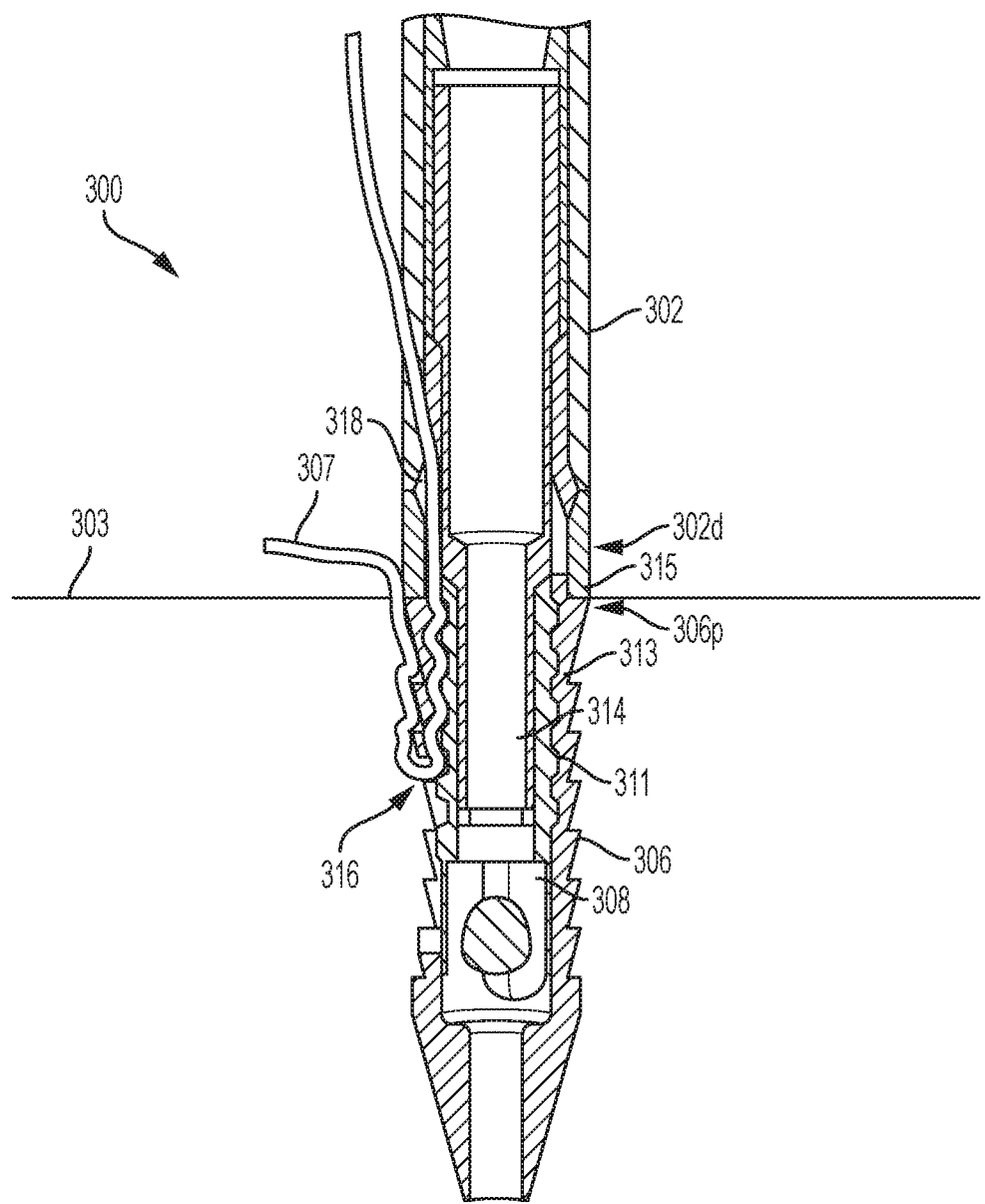
FIG. 4 is a perspective, partially cross-sectional view of a portion of the surgical system of FIG. 3.

FIGS. 3 and 4 illustrate another embodiment of a surgical system 300. The surgical system 300 can be configured and used similar to the system 100 (FIGS. 1-2H), though it has some variations. The surgical system 300 can include a cannulated guide 302, an implantable suture anchor including a cannulated sheath 306 and a screw 308, a first driver shaft or driver 312, and a second driver shaft or driver 314.

The guide 302 has a lumen 310 extending therethrough that allows other components to pass to a suture insertion site. The sheath 306 has a lumen 320 extending therethrough. As shown in FIG. 3, the first driver 312 is configured to be removably received within the lumen 310 of the guide 302 such that a distal tip 312d thereof extends beyond a distal end of the sheath 306. The second driver 314, shown in FIG. 4, is configured to be removably received within the lumen 310 of the guide 302 after the first driver 312 is removed from the lumen 310. The second driver 314 is coupled to the screw 308 and is thus configured to insert the screw 308 into a lumen 320 of the sheath 306.

As shown in FIG. 3, the sheath 306 has a first side opening 316 and the guide 302 has a second side opening 318. Similar to the openings 116, 118 (FIGS. 1 and 2A), the openings 316, 318 are configured to receive a suture therethrough. The sheath 306 can have external threads 309 or other bone-engaging features formed thereon. The lumen 320 of the sheath 306 is configured to receive the screw 308 when the first driver 312 has been separated from the sheath 306 and removed from the guide 302. In some embodiments, a distal end 302d of the guide 302 can be releasably coupled to a proximal end 306p of the sheath 306 via one or more mating features. For example, as shown in FIG. 4, the distal end 302d of the guide 302 can have one more protrusions 315 configured to releasably mate with complementary openings formed at proximal end 306p of the sheath 306. Any other mating features can be implemented.

FIG. 3 illustrates the sheath 306 coupled distally to the guide 302, and illustrates the guide 302 and the sheath 306 having the first driver shaft 312 extending through the lumens 310, 320, respectively. Similar to the method discussed above in connection with the surgical system 100 (FIGS. 2A-2H), the surgical system 300 can be used in a method for performing a surgical repair that includes loading the system 300 with a suture (e.g., a suture 307 shown in FIG. 4), inserting the distal end 312d of the first driver 312 into a bone to create a bone hole into which the distal end 312d is then driven further to deliver the sheath 306 into the bone hole. The first driver 312 can then be separated from the sheath 306 and removed from the guide 302.

FIG. 4 shows the second driver 314 having the screw 308 coupled thereto inserted into the lumen 320 of the sheath 306 and the lumen 310 of the guide 302. The screw 308 can have an external thread 311 or other bone-engaging feature formed thereon configured to engage with a corresponding thread formed on an interior wall defining the lumen 320 of the sheath 306, as shown in FIG. 4. The second driver 314 can be used, for example, similar to the second driver 114 of the surgical system 100. FIG. 4 illustrates the suture 307 (which can be multiple sutures) that can be coupled to the system 300 so as to pass through the first side opening 316 in the sheath 306, the lumen 320 of the sheath 306, the lumen 310 of the guide 302, and the second side opening 318 in the guide 302. In this way, the suture 307 can be secured between a bone 303 and an outer wall of the sheath 306 and between an inner wall of the sheath 306 and an outer wall of the screw 308.

Surgical systems used to attach soft tissue to bone without the need to tie knots can have various configurations. In some systems, a plug or screw can be configured to be move distally to engage with a sheath. However, in some embodiments, the screw can be configured to be moved proximally. The surgical system can vary in any other ways.

Figure 5:
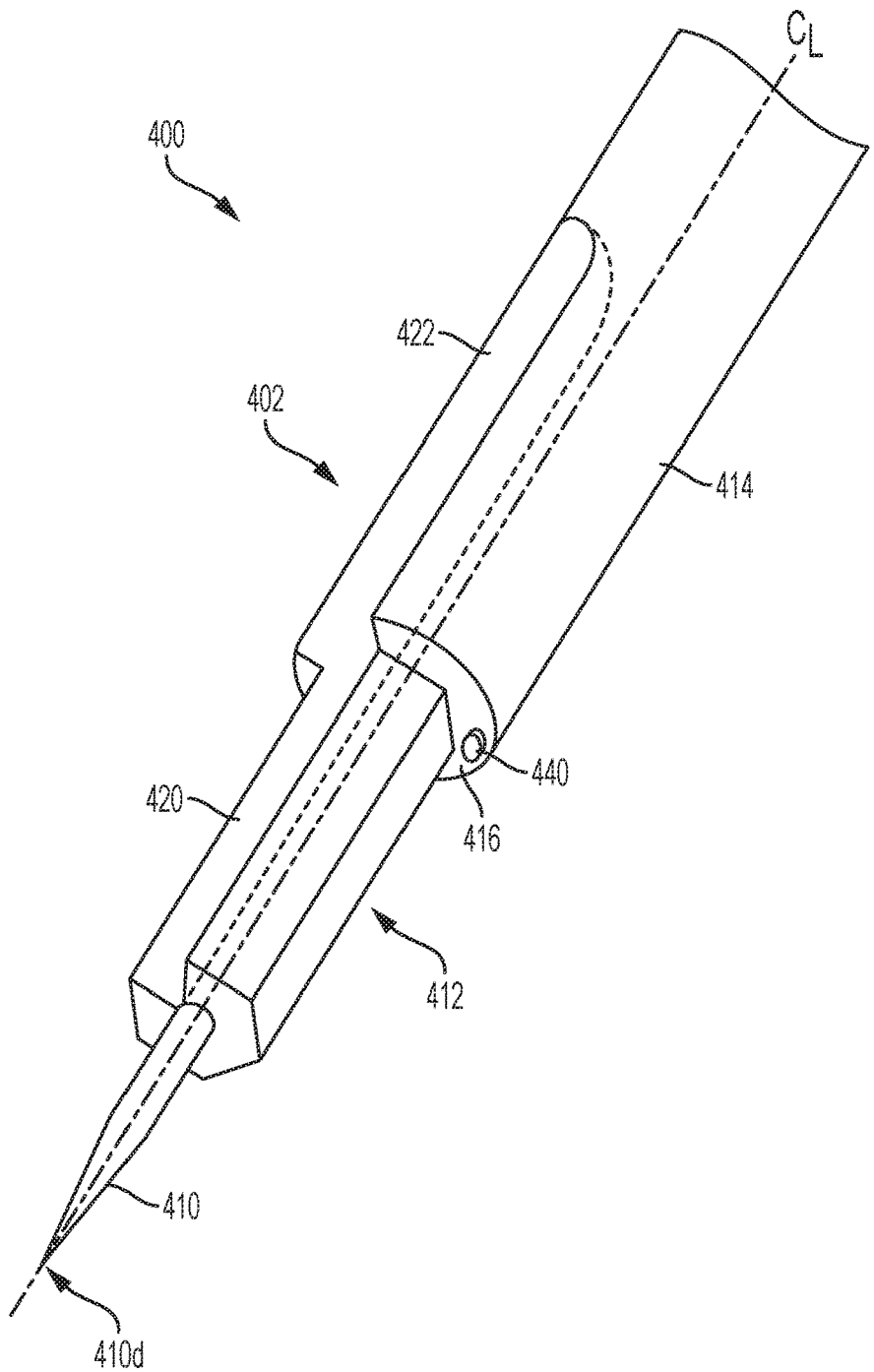
FIG. 5 is a perspective, partially transparent view of a distal portion of a driver device of another embodiment of a surgical system.
Figure 6:
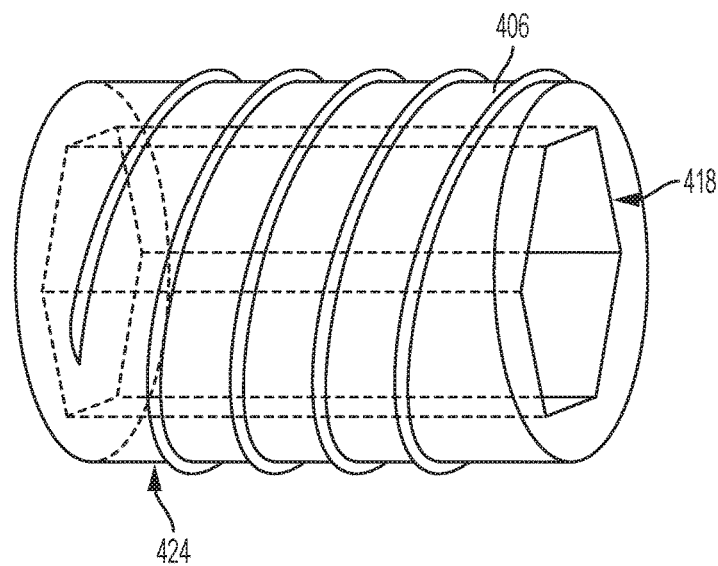
FIG. 6 is a perspective, partially transparent view of one embodiment of a plug.

FIGS. 5-8D illustrate another embodiment of a surgical system 400. The surgical system 400 includes a driver device 402 (FIG. 5) and a suture anchor assembly 403 (FIG. 8A) including a sleeve or sheath 404 (FIG. 7) and a screw or plug 406 (FIG. 6). The system 400 is configured such it has a reduced number of components (as compared to the systems 100, 300, discussed above) and its components can be assembled such that the single driver device 402 is used to deliver the suture anchor assembly 403 into bone. This may simplify the suture anchoring process. Thus, the surgical repair procedure involving reattachment of tissue to bone can be performed in a more time-efficient and less error-prone manner.

The sheath 404 and plug 406 can be cannulated. As shown in FIG. 5, the driver device 402 includes an outer shaft 414 and a driver shaft 412 extending therefrom. The driver device 402 also has an inner or inserter shaft 410 extending through a lumen (not shown) extending through the driver shaft 412 and at least partially through the outer shaft 414. For example, the inserter shaft 410 can be coupled to the outer shaft 414 in a suitable manner or it can extend proximally from the outer shaft 414 be otherwise configured to remain stationary when the driver shaft 412 is rotated.

The inserter shaft 410 terminates at a distal end 410d configured, during use of the driver device 402, to originate a hole in bone. The driver shaft 412 is configured to have the plug 406 releasably coupled thereto such that the driver shaft 412 can be rotated to cause the plug 406 to move proximally into a lumen 416 in the sheath 404. For example, the driver shaft 412 can extend proximally through the outer shaft 414 and it can be coupled to a proximal handle (not shown) configured to rotate the driver shaft 412. Alternatively, in some embodiments, a portion of the outer shaft 414 can be operably coupled to the driver shaft 412 such that the portion can be rotated to cause the driver shaft 412 to rotate. The plug 406 can be configured to be threadably engaged within a lumen in the sheath 404 such that the plug 406 can assist in engagement of the sheath 404 with the bone.

In the illustrated example, at least a portion of an outer wall of the driver shaft 412 extending from the outer shaft 414 has a hexagonal shape such that the driver shaft 412 in the form of a male hexagonal feature is configured to mate with a complementary-shaped interior wall defining a lumen 418 extending through the plug 406. Thus, as shown in FIG. 6, the plug's lumen 418 is hexagonally shaped. It should be appreciated however that the driver shaft 412 in the form of a hex and the complementary-shaped lumen 418 in the plug 406 are shown by way of example only, as the driver shaft 412 and at least a portion of the lumen 418 can have a square or any other configuration. Any suitable torsion-transmitting features can be formed on the driver shaft 412 and in the lumen 418.

As shown in FIG. 5, the driver shaft 412 and the outer shaft 414 have slots 420, 422 formed in side walls thereof, respectively. The slots 420, 422 are configured so as to communicate and align with one another and with an opening 405 formed in a side wall of the sheath 404, as discussed below. The outer shaft 414 has a distal shoulder 416 and in the assembled configuration shown in FIG. 8A, the sheath 404 abuts the distal shoulder 416.

The plug 406 can have any suitable configuration. In the example illustrated, as shown in FIG. 6, the plug 406 is generally cylindrical and, as mentioned above, it has the hexagonally-shaped lumen 418. An outer wall of the plug 406 has one or more threads 424 formed thereon configured to engage corresponding threads formed on an interior wall defining the lumen 426 extending longitudinally through the sheath 404.

Figure 7:
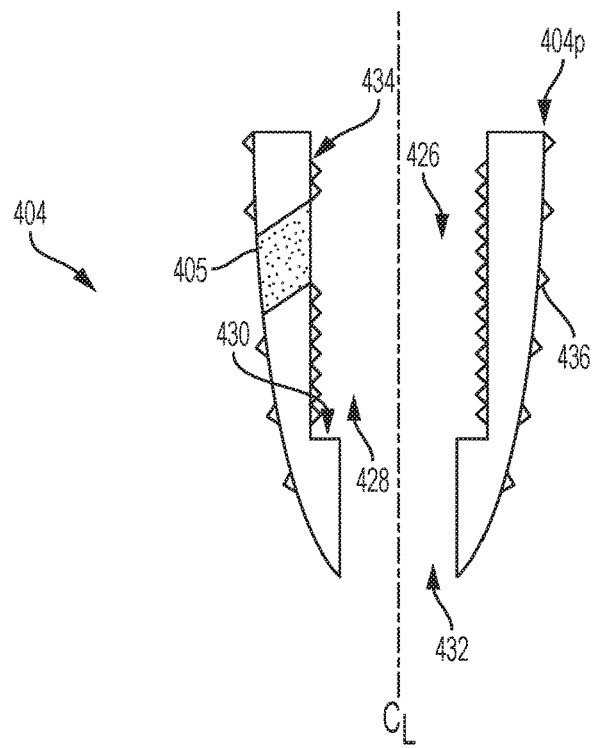
FIG. 7 is a perspective, cross-sectional view of one embodiment of a sheath.

The sheath 404 can also have any suitable configuration. In the example illustrated, as shown in FIG. 7, the sheath 404 has the lumen 426 that has a distal portion 432 and a proximal portion 428 having an inner shoulder 430. The proximal portion 428 has a thread 434 formed thereon that corresponds to the thread 424 formed on the plug 406. The outer wall of the sheath 404 can have one or more bone engaging features 436, such as, e.g., ribs, threads, etc. As shown in FIG. 7, the sheath 404 also has the opening 405 formed through a side wall thereof.

Figure 8A:
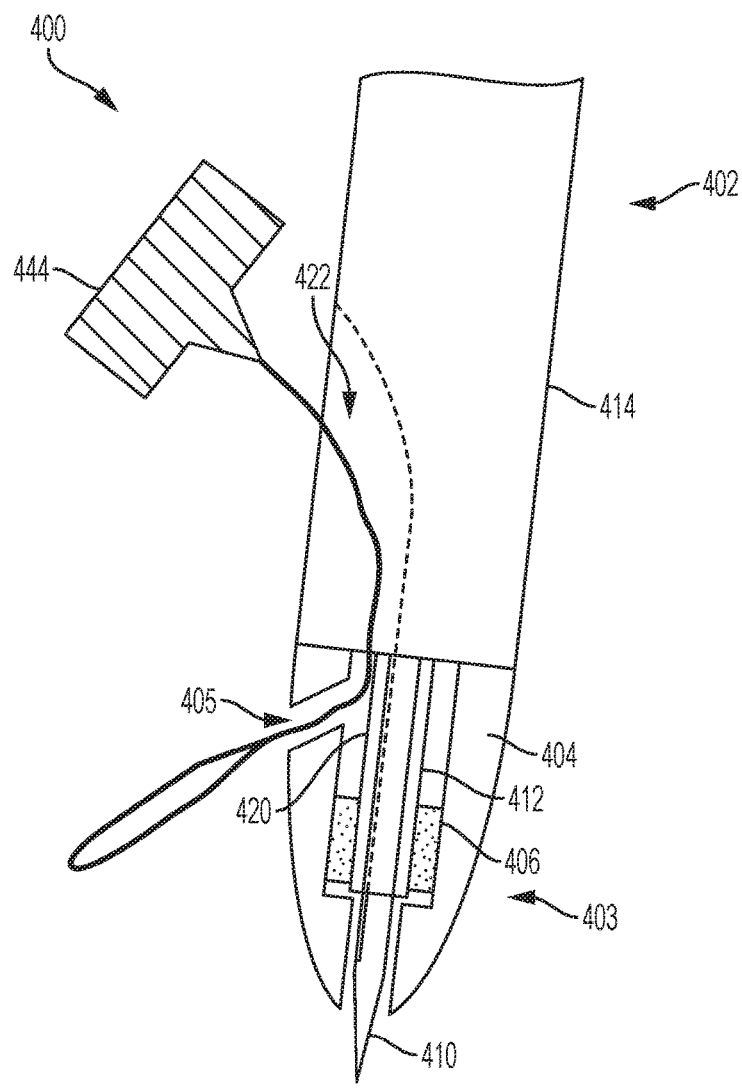
FIG. 8A illustrates the surgical system including the driver device of FIG. 5, the plug of FIG. 6, and the sheath of FIG. 7.

In the assembled configuration, as shown in FIG. 8A, the sheath 404 is positioned such that its proximal end abuts the shoulder 416. The plug 406 can be pre-coupled to the sheath 404 such that the plug's distal end abuts the shoulder 430 in the inner lumen 426 of the sheath 404. The plug 406 is also coupled to the driver shaft 412. In some embodiments, the outer shaft 414 can have one or more mating features for releasably mating with the sheath 404. For example, the shoulder 416 of the outer shaft 414 can has one or more protrusions 440 or other features configured to releasably mate with corresponding mating features formed on a proximal end 404p of the sheath 404. For example, the sheath 404 can have openings or other feature(s) (not shown) configured to mate with the features formed on the shoulder 416 of the outer shaft 414.

FIG. 8A shows that a threader tab or loop 444 can be used to pass at least one suture through the opening 405 in the sheath 404 and along the slots 420, 422 in the driver shaft 412 and the outer shaft 414. In some embodiments, the system 400 can include one or more sutures preloaded on the driver device 402.

Figure 8B:
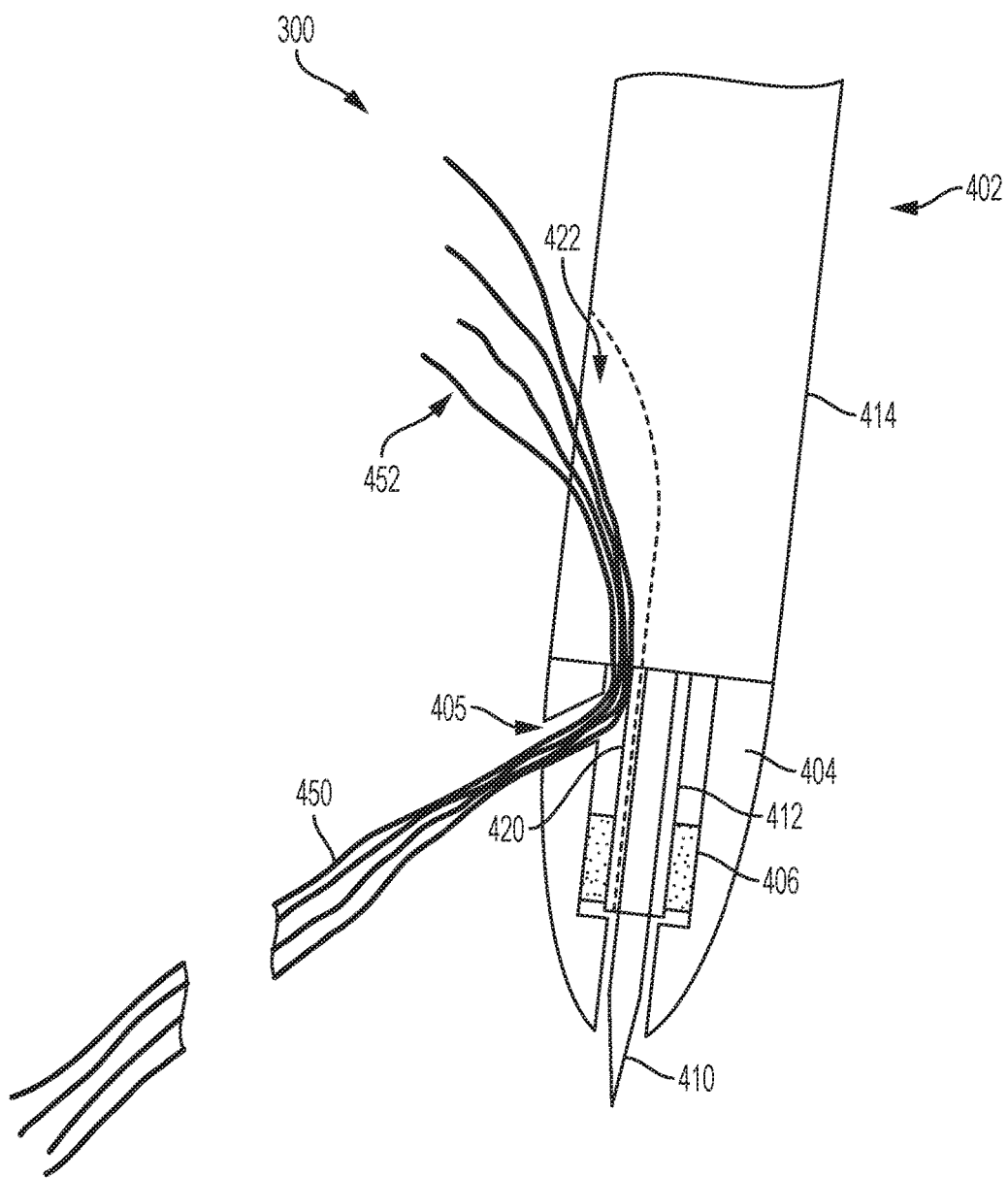
FIG. 8B illustrates the surgical system of FIG. 8A, showing a suture coupled to the system.
Figure 8C:
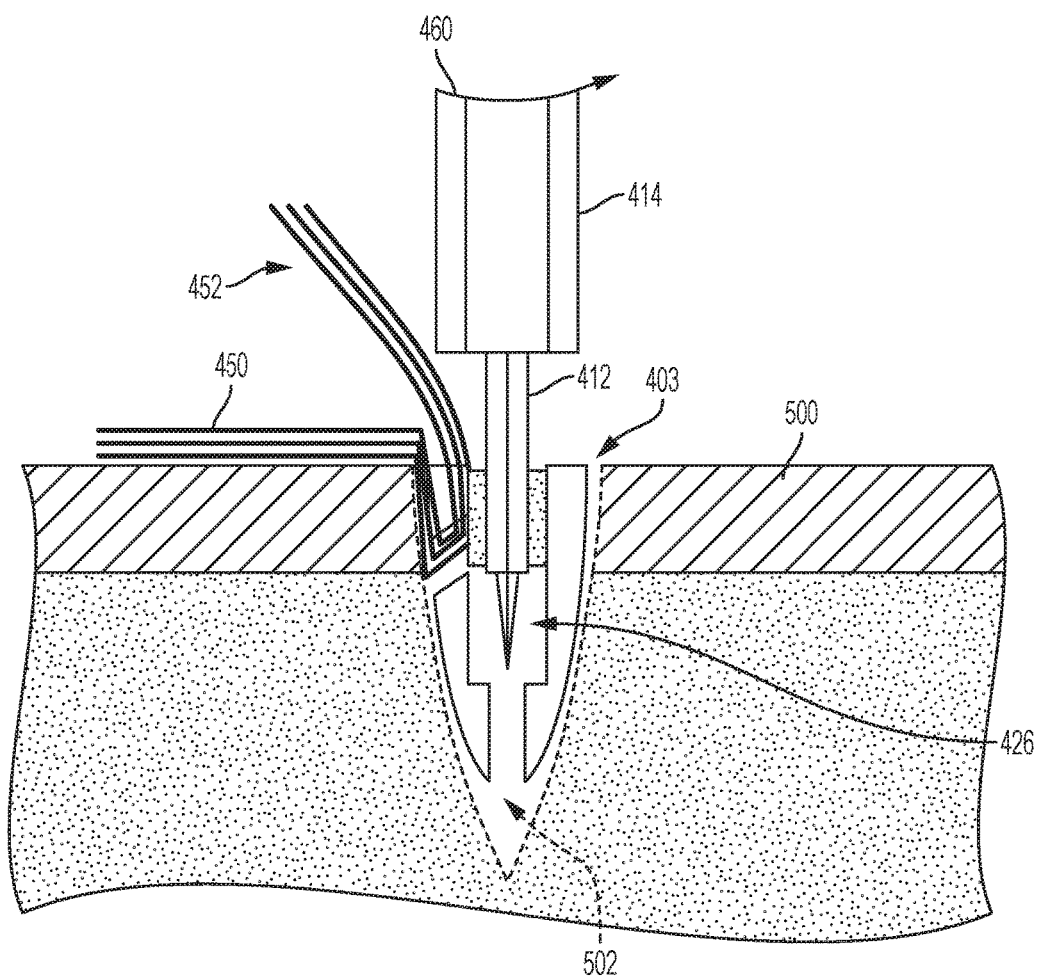
FIG. 8C illustrates the surgical system of FIG. 8B, showing the system driven distally into bone.
Figure 8D:
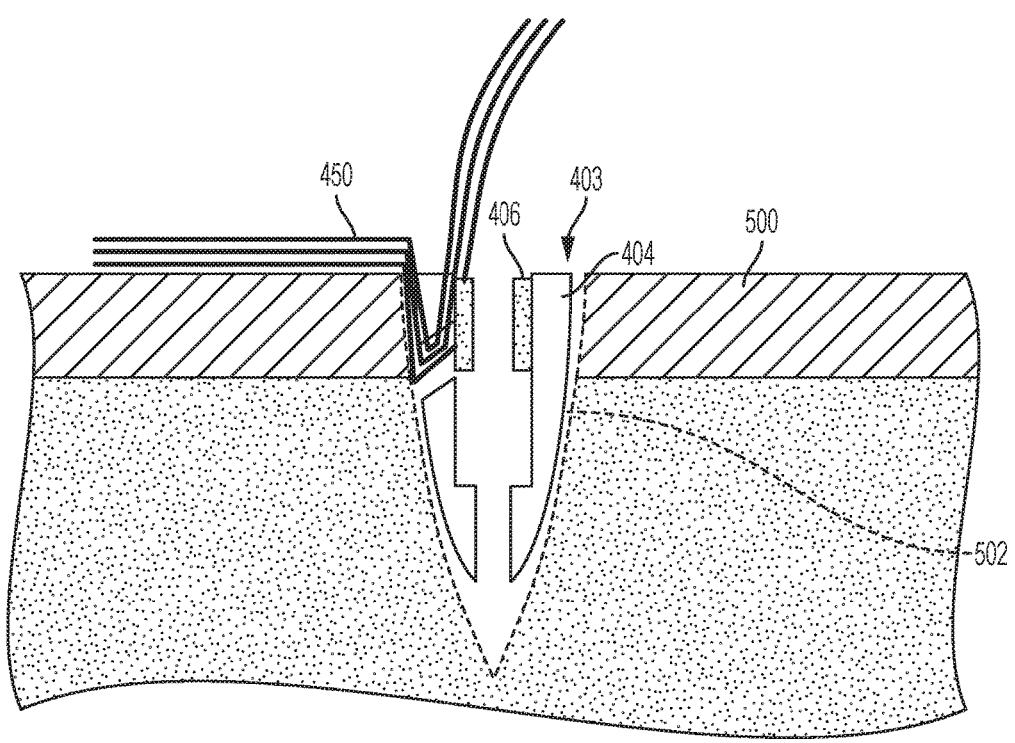
FIG. 8D illustrates the surgical system of FIG. 8C, showing the suture secured.

FIGS. 8B-8D illustrate a method for performing a surgical repair using the system 400 assembled as shown in FIG. 8A. As shown in FIG. 8B, sutures 450 coupled to tissue or an anchor (not shown) can be passed (e.g., using the threader loop 444) through the opening 405 in the sheath 404 and into the slots 420, 422 in the driver shaft 412 and the outer shaft 414 such that terminal end portions 452 of the sutures 450 extend from the slot 422 of the outer shaft 414. The distal tip of the inserter shaft 410 is configured to penetrate bone 500. Thus, the driver device 402 having the plug 406 (and the sheath 404 coupled to the plug 406) removably coupled thereto can be used to initiate a bone hole at a desired location when it is driven into the bone 500 such that the distal end 410d of the inserter shaft 410 penetrates the bone 500. A mallet or other suitable instrument (not shown) can be used to apply force to the proximal end of driver device 402 to drive the distal end 410d of the inserter shaft 410 further into the bone hole which is widened by the distal portion of the sheath 404. The sheath 404 with the plug 406 pre-loaded thereon is thus delivered to the bone 500 to an appropriate depth. Thus, as shown in FIG. 8C, in the illustrated embodiment, the sheath 404 sits in a bone hole 502 in a bone 500 such that the proximal end of the sheath 404 sits just below the surface of the bone 500. However, in other embodiments, the proximal end of the sheath 404 can sit at or above the surface of the bone 500.

FIG. 8C illustrates, by an arrow 460, that the driver shaft 412 having the plug 406 coupled thereto can be rotated such that the rotation of the driver shaft 412 causes the plug 406 to move proximally within the lumen 426 in the sheath 404 so as to be disposed such that the plug's proximal end is at or near the proximal end of the sheath 404. The slots 420, 422 are not shown in FIG. 8C. Tension can be maintained on the sutures 450 during insertion of the device 402 into the bone and during rotation of the driver shaft 412. FIG. 8C illustrates the system 400 at the state in which the plug 406 has been driven proximally and within the sheath's lumen 426 such that the plug 406 occludes the opening 405 in the sheath 404. As a result, the sutures 450 become engaged between the bone 500 and an outer wall of the sheath 404 and between an inner wall of the sheath 404 (in the lumen 426) and an outer wall of the plug 406, which is also shown in FIG. 8C. Once the plug 406 is disposed within the sheath 404 so as to secure the sutures 450, the driver device 402 can be separated from the suture anchor assembly 403, for example, the driver device 402 can be pulled out proximally, as also shown in FIG. 8C. It should be appreciated that rotating the driver shaft 412 to move the plug 406 proximally within the sheath's lumen 426 can be performed before the driver device 402 is separated from the suture anchor assembly 403. FIG. 8D shows the suture anchor assembly 403 inserted into the hole 502 in the bone 500 to thereby anchor the sutures 550 to the bone 500. If desired, the terminal ends 452 of the suture 450 can be trimmed.

It should be appreciated that the surgical system 400 can vary in different ways. For example, in some embodiments, the surgical system can be configured such that the driver shaft can be rotated to cause the plug to be driven distally within the sheath's lumen. Other variations can be implemented additionally or alternatively.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the shafts, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the components of the system described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred the components are sterilized. This can be done by any number of ways known to those skilled in the art including beta or gamma radiation, ethylene oxide, steam, and a liquid bath (e.g., cold soak).

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A method for performing a surgical repair, comprising:
   inserting a distal end of a first driver into a bone, the first driver extending through a proximal channel in a sheath portion of an implantable suture anchor and through a lumen of a guide removably coupled proximally to the sheath portion, the sheath portion and the guide having a suture extending through the lumen and the proximal channel and between first and second openings extending through sides of the sheath portion and the guide, respectively, wherein the suture anchor also includes a screw portion; and
   removing the first driver from the proximal channel and the lumen, and then inserting a distal driver member of a second driver through the lumen of the guide and into the proximal channel of the sheath portion, the distal driver member having the screw portion coupled distally thereto, wherein the insertion causes the screw portion to be driven distally into the proximal channel and the suture to be secured between an outer wall of the sheath portion and the bone and between an outer wall of the screw portion and an inner wall of the sheath portion.

2. The method of claim 1, wherein inserting the distal driver member through the lumen and into the proximal channel of the sheath portion comprises rotating the second driver to cause the distal driver member to insert the screw portion into the proximal channel of the sheath portion.

3. The method of claim 1, wherein the suture is engaged using the implantable suture anchor such that the suture extends between the bone and an outer wall of a proximal portion of the sheath portion, along a proximal inner wall of the first opening, and between an inner wall of the proximal portion of the sheath portion and an outer wall of the screw portion.

4. The method of claim 1, further comprising tensioning the suture while inserting the distal end of the first driver into the bone.

5. The method of claim 1, further comprising tensioning the suture while inserting the distal driver member through the lumen of the guide and into the proximal channel of the sheath portion.

6. The method of claim 1, wherein the screw portion being received within the proximal channel of the sheath portion causes expansion of the sheath portion.

* * * * *